United States Patent
Miller et al.

(10) Patent No.: US 8,375,952 B2
(45) Date of Patent: Feb. 19, 2013

(54) DEVICE AND METHOD FOR UNILATERAL LUNG VENTILATION

(75) Inventors: Thomas L. Miller, Wilmington, DE (US); Thomas H. Shaffer, Chadds Ford, PA (US); Mary Theroux, Newark, DE (US); John Bernardi, Swedesboro, NJ (US)

(73) Assignee: The Nemours Foundation, Jacksonville, FL (US)

( * ) Notice: Subject to any disclaimer, the term of this patent is extended or adjusted under 35 U.S.C. 154(b) by 1230 days.

(21) Appl. No.: 12/228,019

(22) Filed: Aug. 8, 2008

(65) Prior Publication Data

US 2009/0038621 A1 Feb. 12, 2009

Related U.S. Application Data

(60) Provisional application No. 60/964,151, filed on Aug. 9, 2007.

(51) Int. Cl.
*A61M 16/00* (2006.01)
*A62B 7/00* (2006.01)
*A62B 9/06* (2006.01)

(52) U.S. Cl. ......... 128/207.14; 128/200.26; 128/204.18; 128/207.15

(58) Field of Classification Search ............. 128/200.26, 128/204.18, 207.14, 207.15
See application file for complete search history.

(56) References Cited

U.S. PATENT DOCUMENTS

| | | | | | |
|---|---|---|---|---|---|
| 4,446,864 A | * | 5/1984 | Watson et al. | ........... | 128/207.14 |
| 4,453,545 A | * | 6/1984 | Inoue | ...................... | 128/207.15 |
| 4,498,473 A | * | 2/1985 | Gereg | ...................... | 128/207.15 |
| 4,955,375 A | * | 9/1990 | Martinez | ................. | 128/207.15 |
| 5,291,882 A | * | 3/1994 | Makhoul et al. | ......... | 128/207.14 |
| 5,372,131 A | * | 12/1994 | Heinen, Jr. | ............... | 128/207.15 |
| 5,562,608 A | * | 10/1996 | Sekins et al. | .................... | 604/20 |
| 5,588,424 A | * | 12/1996 | Insler et al. | .............. | 128/207.15 |
| 5,660,175 A | * | 8/1997 | Dayal | ...................... | 128/207.15 |
| 6,287,290 B1 | * | 9/2001 | Perkins et al. | ............... | 604/516 |
| 6,443,156 B1 | * | 9/2002 | Niklason et al. | ......... | 128/207.14 |
| 6,520,183 B2 | * | 2/2003 | Amar | ....................... | 128/207.14 |
| 6,550,475 B1 | * | 4/2003 | Oldfield | ................... | 128/200.26 |
| 6,929,637 B2 | * | 8/2005 | Gonzalez et al. | .......... | 604/890.1 |
| 7,121,280 B2 | * | 10/2006 | Kyle, Jr. | .................... | 128/207.14 |
| 2003/0154988 A1 | * | 8/2003 | DeVore et al. | ............ | 128/207.15 |
| 2004/0144387 A1 | * | 7/2004 | Amar | ....................... | 128/207.14 |
| 2006/0090761 A1 | * | 5/2006 | Kurrus | ...................... | 128/207.15 |
| 2007/0221229 A1 | * | 9/2007 | Rahaghi et al. | .......... | 128/207.14 |

* cited by examiner

*Primary Examiner* — Oren Ginsberg

(74) *Attorney, Agent, or Firm* — Drinker Biddle & Reath LLP

(57) ABSTRACT

A system for unilateral lung ventilation includes an endotracheal tube and a blocking device for blocking the bronchus of a non-ventilated lung to prevent a ventilation medium from entering the lung. The blocking device includes an inflatable member supported by a catheter having an inflation lumen for inflating the inflatable member. The catheter includes at least one lung treatment lumen for delivering a therapeutic agent to the non-ventilated lung. An inner channel within the main channel and a side branch provide a guideway for the blocking device within the tube. A valve may be included to close the side branch when the blocking device is removed from the inner channel for parallel flow of ventilating gas in the main and inner channels. A method of using the system provides for ventilation/perfusion (V/Q) matching by respectively delivering cooled air and nitric oxide to the non-ventilated and ventilated lungs.

14 Claims, 1 Drawing Sheet

DEVICE AND METHOD FOR UNILATERAL LUNG VENTILATION

FIELD OF THE INVENTION

The present invention relates to lung ventilation and, more particularly, to a device and method for unilateral lung ventilation.

BACKGROUND OF THE INVENTION

Children and adults undergoing thoracic surgeries often require unilateral lung ventilation and/or anesthesia. Specially designed endotracheal tube setups are used by anesthesiologists to facilitate unilateral ventilation procedures. Multiple endotracheal tube systems are currently in use that are specifically designed to either intubate the mainstem bronchus of the ventilated lung or to block the mainstem bronchus of the non-ventilated lung. However, each of these tube designs has specific limitations.

The tubes designed to intubate the mainstem bronchus of the ventilated lung include two fixed channels within the tube. When the procedure is completed and the patient is restored to bilateral ventilation, the presence of the two fixed channels undesirably limits airflow in and out of the lung by increasing resistance, thus adversely altering the mechanics. Therefore it is desirable to re-intubate the patient with a standard endotracheal tube following completion of the surgical procedure utilizing unilateral lung ventilation. However, repeated intubations are known to result in trauma to the epithelial lining of the airways.

It is also known to use a standard endotracheal tube to perform unilateral lung ventilation by passing a balloon catheter through a standard endotracheal tube such that the balloon catheter is inserted into the bronchus of the lung to be blocked. The balloon is subsequently inflated. The catheter contains a single lumen for access to the non-ventilated lung. This use of the balloon catheter with the standard endotracheal tube eliminates the need for re-intubation of the patient associated with the use of tubes specifically adapted to intubate the mainstem bronchus of a lung. However, the passage of the balloon catheter through the standard endotracheal tube places the catheter within the main lumen of the standard tube, thereby disrupting laminar airflow in the main lumen. Also, the balloon catheter can move around within the main lumen because it is not constrained with respect to the main lumen. This movement of the catheter contributes to the need for periodic repositioning of the balloon in the blocked bronchus, which can be a source of trauma to the epithelial tissues. Furthermore, the catheter accessing the non-ventilated lung is not thermally isolated from the main orifice of the endotracheal tube, which can be a limitation for a potential therapy to be described herein.

During unilateral lung ventilation procedures, the unventilated lung is collapsed and sometimes manually moved from the surgical field. Resulting contusions, alveolar collapse and atelectasis are known to contribute to lung inflammation. Moreover, it is difficult to maintain arterial oxygen saturation because of the extreme ventilation/perfusion (V/Q) mismatch that results when one lung receives no ventilation. In an effort to maintain blood oxygen levels when there is such dramatic V/Q mismatch, elevated inspired oxygen levels are supplied to the ventilated lung. Such high oxygen levels, however, are known contributors to lung disease. Laboratory studies indicate that lung function is hampered following re-recruitment of a collapsed lung after only 30 minutes of unilateral lung ventilation. The studies also demonstrate that unilateral lung ventilation using conventional techniques has a dramatic impact on lung morphology.

What is needed is a ventilation technique aimed at attenuating or eliminating the alterations in lung function and inflammation noted when bilateral ventilation is restored following a unilateral ventilation procedure. More particularly, what is needed is a device and method for unilateral lung ventilation that provides for delivery of therapeutic agents and/or interventions to both the ventilated and the non-ventilated lung before, during and following the procedure. The focus is to optimize V/Q matching during the unilateral ventilation procedure and to treat the lung for the inflammatory response to the associated traumas.

SUMMARY OF THE INVENTION

According to one aspect of the invention, a system for unilateral lung ventilation comprising an endotracheal tube and a blocking device. According to one exemplary embodiment, the endotracheal tube includes a main channel for delivering a ventilating gas to the trachea of a patient. The blocking device includes an inflatable member having inflated and deflated conditions and adapted for inflation within the mainstem bronchus of a non-ventilated one of a patient's lungs such that the ventilating gas from the endotracheal tube is prevented from entering the non-ventilated lung. The blocking device also includes an elongated catheter supporting the inflatable member and having an inflation lumen adapted to deliver a gas/fluid volume to the inflatable member. The catheter further includes at least one lung treatment lumen adapted for delivery of a treatment agent into the non-ventilated lung when the inflatable member is inflated within the mainstem bronchus of the non-ventilated lung.

According to another exemplary embodiment, the endotracheal tube has a primary wall defining a main channel for delivering a ventilating gas to the trachea of a patient and a secondary wall defining an inner channel located within the main channel. The blocking device includes an inflatable member having inflated and deflated conditions and adapted for inflation within the mainstem bronchus of a non-ventilated one of the lungs of the patient such that the ventilating gas from the endotracheal tube is prevented from entering the non-ventilated lung. The blocking device also includes an elongated catheter supporting the inflatable member and adapted to deliver a gas/fluid volume to the inflatable member. The inner channel of the endotracheal tube is adapted to receive the catheter and the inflatable member when the inflatable member is in the deflated condition to define a guideway to facilitate passage of the catheter and the inflatable member to a distal end of the endotracheal tube.

The endotracheal tube may also include a side branch connected to a primary wall of the endotracheal tube that defines the main channel. The side branch is adapted for receipt of the catheter and the inflatable member of the blocking device to direct the catheter and the inflatable member into the inner channel of the tube. The endotracheal tube may also include a valve adjacent a junction between the side branch and the primary wall adapted to substantially close an end of the side branch at the junction when the blocking device is removed from the inner channel. The closure of the side branch in this manner facilitates parallel flow of a ventilating gas through the endotracheal tube in both the main channel and the inner channel of the tube when the blocking device is removed from the endotracheal tube. When the blocking device is in place, the valve system will close to the top of the side channel, isolating the catheter suspending the blocking device from the warm ventilating gas being delivered through the main orifice of the endotracheal tube.

According to another aspect of the invention, a method of unilaterally ventilating a patient using the system is provided. The method comprises the steps of inserting the endotracheal tube into the patient via the patient's mouth such that a distal end of the tube is received in the trachea of the patient and inserting the blocking device into the patient via the patient's mouth with the inflatable member in the deflated condition such that the inflatable member is received by the mainstem bronchus of the non-ventilated lung of the patient. The method also includes the steps of delivering inflation gas/fluid to the inflatable member via the inflation lumen of the catheter to inflate the inflatable member to the inflated condition and delivering a ventilating gas into the trachea of the patient via the main channel of the endotracheal tube to ventilate the ventilated lung. The method further includes the step of delivering a therapeutic agent to the non-ventilated lung via the at least one lung treatment lumen. The therapeutic agent may include cooled air or a preservative agent such as an anti-inflammatory agent.

The method may include the further step of delivering a therapeutic agent to the ventilated lung. According to one presently preferred embodiment, the therapeutic agent delivered to the non-ventilated lung is cooled air and the therapeutic agent delivered to the ventilated lung is nitric oxide for maintaining ventilation/perfusion (V/Q) matching during the unilateral ventilation.

DESCRIPTION OF THE INVENTION

Figure 1:
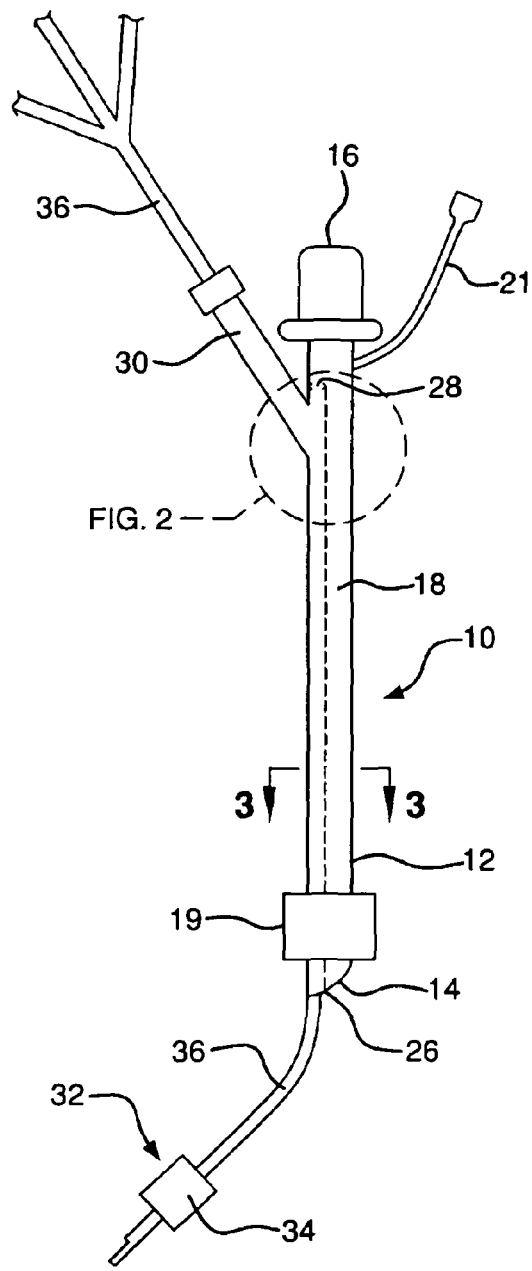
FIG. 1 is side view of a system for unilateral lung ventilation according to an exemplary embodiment of the invention.
Figure 2:
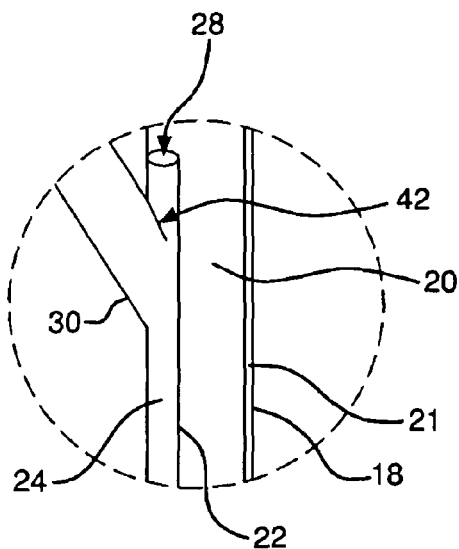
FIG. 2 is an enlarged detail view of a portion of the system of FIG. 1.
Figure 3:
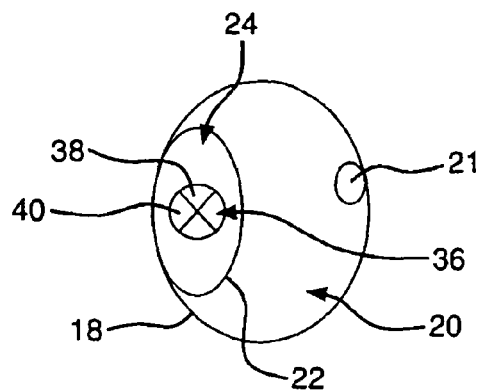
FIG. 3 is a sectional view of the system of FIG. 1 taken along the lines 3-3 in FIG. 1.

Referring to the drawings, where like numerals identify like elements, there is shown in FIGS. 1 through 3 a system 10 for unilateral lung ventilation according to an exemplary embodiment of the invention. As described below in greater detail, the system 10 provides for blockage of a non-ventilated lung during ventilation of the other lung while simultaneously permitting delivery of therapeutic agents into the non-ventilated lung via a thermally isolated catheter.

Referring to FIG. 1, the system 10 includes an endotracheal tube 12 having a distal end 14 and an opposite proximal end 16. The endotracheal tube 12 includes a primary wall 18 defining a main channel 20. The endotracheal tube 12 is adapted for insertion of the distal end 14 of the tube 12 into a patient's trachea via the patient's mouth. Preferably, the primary wall 18 of the endotracheal tube 12 is made from a flexible material in a similar manner as standard endotracheal tubes to facilitate insertion of the tube 12 into a patient's trachea. The tube 12 includes an inflatable cuff 19 adjacent the distal end 14 of the tube 12 to secure the tube into the patient's trachea. The inflatable cuff 19 communicates with an inflation lumen 21 for delivering an inflation medium (e.g., a fluid/gas) to the cuff 19 for inflating the cuff. As shown, the inflation lumen 21 extends to an exterior of the tube 12 adjacent the proximal end 16 of the tube 12 to facilitate the introduction of an inflation medium into the inflation lumen 21.

The endotracheal tube 12 also includes a secondary wall 22 defining a inner channel 24 within the main channel 20 of the tube 12. Referring to FIG. 3, the secondary wall 22 of tube 12 is connected to the primary wall 18 of tube 12 at an inner surface of the primary wall 18. As shown, the secondary wall 22 is arranged such that the inner channel 24 defined by the secondary wall 22 is located at one side of the main channel 20 defined by the primary wall 18 and is limited in size compared to the main channel 20. Preferably, the primary and secondary walls 18, 22 are integrally formed by molding the walls 18, 22 from a moldable material. As illustrated by the broken line in FIG. 1, the inner channel 24 defined by the secondary wall 22 of tube 12 extends along a major length of the primary wall 18 and has opposite ends 26, 28 respectively located at the distal end 14 of tube 12 and at a point that is located at a distance from the proximal end 16 of the tube 12.

The endotracheal tube 12 also includes a side branch 30 located externally of the main channel 20 and connected to the primary wall 18 of the tube 12 at a location between the opposite ends 26, 28 of the inner channel 24. As shown in FIGS. 1 and 2, the side branch 30 of tube 12 is preferably oriented at an oblique angle with respect to the primary wall 18 of tube 12.

Referring again to FIG. 1, the unilateral lung ventilation system 10 includes a blocking device 32 adapted to block the mainstem bronchus of a non-ventilated one of the lungs of a patient, thereby preventing a gas (e.g., air) that is discharged from the main channel 20 into the trachea of the patient from entering the non-ventilated lung. The depicted blocking device 32 includes a balloon mechanism 34 carried by an elongated multi-lumen catheter 36. The balloon mechanism 34 is adapted to inflate and deflate when a fluid/gas is respectively delivered to and removed from the balloon mechanism 34 via one specified lumen of the elongated catheter 36. When inflated within the mainstem bronchus of the non-ventilated lung, the balloon mechanism 34 is adapted to close off the bronchus, thereby preventing ventilating gas discharged into the trachea of the patient from the distal end 14 of the tube 12 from entering the non-ventilated lung from the trachea. The deflated condition of the balloon mechanism 34 facilitates insertion of the balloon mechanism 34 into the mainstem bronchus of the non-ventilated lung by feeding the catheter 36, and the balloon mechanism 34 carried thereon, through the endotracheal tube 12 as described below in greater detail. Referring to FIG. 3, the catheter 36 of the blocking device 32 is preferably a triple lumen catheter having three inner lumens 40 defined within an outer catheter tube 38. As described below, the construction of the depicted blocking device 32 functions to prevent the ventilating gas from entering the non-ventilated lung while permitting a ventilation medium (e.g., gas or fluid) from a separate source, or a drug therapy, to be introduced into the non-ventilated lung via the catheter 36 of the blocking device 32.

Referring again to FIG. 1, the blocking device 32 is directed into the mainstem bronchus of the non-ventilated lung by feeding the catheter 36 and balloon mechanism 34 into, and through, the inner channel 24 via the side branch 30. In this manner, the side branch 30 and inner channel 24 provide a guideway through the endotracheal tube 12 for the blocking device 32. The oblique-angle orientation between the side branch 30 and the primary wall 18 of the endotracheal tube 12 facilitates the passage of the catheter 36 and balloon mechanism 34 from the side branch 30 into the inner channel 24. In addition to serving as part of a guideway during passage of the catheter 36 and balloon mechanism 34 through the tube 12, the presence of the inner channel 24 within the main channel 20 also functions to isolate the catheter 36 from the main channel 20. This isolation desirably limits interference by the catheter 36 with an airstream directed through the main channel 20 that might otherwise occur if the catheter were merely passed through the main channel in an unrestrained manner. The presence of the inner channel 24, therefore, desirably limits airstream turbulence by the catheter 36, thereby promoting a laminar airflow through the main channel 20 of the endotracheal tube 12.

Referring to FIG. 2, the end 28 of the inner channel 24 is open such that the inner channel 24 communicates with the main channel 20 at the end 28. As shown, the endotracheal tube 12 preferably includes a valve mechanism 42 within the interior of the tube 12 located adjacent the juncture between the side branch 30 and the primary wall 18. The valve mechanism 42 is preferably adapted such that an end of the side branch 30 adjacent the juncture is normally closed by the valve mechanism 42. In this manner, the inner channel 24 will be open along its length absent placement of a catheter 36 into the inner channel 24 via the side branch 30. In this manner, a gas (e.g., air) that is introduced into the main channel 20 through the proximal end of the tube 12 will enter, and pass through, both the main channel 20 and the inner channel 24 when the catheter 36 of blocking device 32 is removed from the endotracheal tube 12. This desirably maximizes and promotes laminar airflow through the endotracheal tube 12 when the blocking device 32 is removed following a surgical procedure utilizing the unilateral lung ventilation.

The valve mechanism 42 is adapted to open the end of the side branch 30 when the blocking device 32 is fed into the side branch 30 and contacts the valve mechanism 42, thereby permitting passage of the blocking device 32 through the tube guideway. Preferably, the valve mechanism 42 will extend substantially across the inner channel 24 when the blocking device 32 has been fed through the guideway such that the end 28 of the inner channel 24 is substantially closed off from the rest of the inner channel 24. Such closure of the inner channel 24 serves to limit passage of a ventilating gas (e.g., air), which has been introduced into the main channel 20, from circulating in the inner channel 24 adjacent the catheter 36. The isolation of the inner channel 24 in this manner desirably insulates the catheter 36 from a gas in the main channel 20, thereby facilitating conveyance of a fluid to the non-ventilated lung via the triple lumen catheter 36 having a temperature that differs from that of the ventilating gas in the main channel 20, in the triple-lumen catheter 36. This feature promotes separate treatment of the non-ventilated lung as described below in greater detail.

The valve mechanism 42 is depicted in FIG. 2 as a simple flap of material which could be formed integrally with the primary wall 18 of the endotracheal tube 12 (e.g., by molding the flap from a moldable material). The invention, however, is not so limited and encompasses other potential valve designs.

As described above, the unilateral lung ventilation system 10 functions to prevent a ventilation medium (e.g., air) discharged into a patient's trachea from the main channel 20 of the endotracheal tube 12 to ventilate one of the patient's lungs from circulating into a non-ventilated lung. The non-ventilated lung is blocked, and thereby isolated from the ventilation medium, when the balloon mechanism 34 of the blocking device 32 is inserted into the mainstem bronchus of the non-ventilated lung and inflated (e.g., by conveying a gas/fluid into the balloon mechanism 34 via one of the lumens 40 of the triple lumen catheter 36). The presence of the additional lumens 40 within the interior of the catheter 36, however, provides for delivery of therapeutic agents, such as described below, into the non-ventilated lung via the catheter while the non-ventilated lung is simultaneously isolated from the ventilating gas being delivered to the other (i.e., ventilated) lung. The relative size of the lumens 40 could vary. For example, it is conceivable that the two additional lumens 40 available to deliver therapeutic agents into the non-ventilated lung have a diameter that is larger than that of the lumen 40 dedicated to conveying the inflation gas/fluid to the balloon mechanism 34.

As described above, a limitation with prior unilateral lung ventilation techniques is that is difficult to maintain arterial oxygen saturation during the procedure because of an extreme ventilation/perfusion (V/Q) mismatch that occurs when one lung receives no ventilation. The present invention provides a method for unilateral lung ventilation utilizing the above-described system 10 in which V/Q matching is maximized throughout the procedure. First, the system 10 is installed in the patient as described above by inserting the endotracheal tube 12 into the trachea of the patient via the patient's mouth, feeding the blocking device 32 through the tube 12 via the guideway to position the balloon mechanism 34 in the mainstem bronchus of the patient, and inflating the balloon mechanism 34 by delivering a gas/fluid to the balloon mechanism via one of the lumens 40 of the catheter 36. Installed in this manner, the system 10 is ready for unilateral ventilation of the ventilated lung by discharging a ventilation medium (e.g., air) from the main channel 20 of the tube 12 into the patient's trachea.

During the unilateral lung ventilation, the method provides for optimized V/Q matching in the following manner. Agents are preferably separately introduced into the ventilated and non-ventilated lungs to maximize V/Q matching. According to one presently preferred embodiment, cold air is delivered to the non-ventilated lung via the catheter 36 while nitrous oxide is simultaneously introduced into the ventilated lung (i.e., in addition to the ventilating gas being supplied). As mentioned above, the construction of the system 10 provides for isolation of the catheter 36 from the ventilating gas because the valve mechanism 42 prevents the ventilating gas from circulating in the inner channel 24 adjacent the catheter 36. This feature desirably facilitates the present V/Q matching method by thermally isolating the cold air within the catheter 36 from the relatively warmer gases being delivered into the trachea from the main channel 20 of tube 12. Absent such isolation, thermal transfer would cause the cold air being delivered to the non-ventilated lung via the catheter 36 to be warmer than desired and the ventilating gas being delivered to the ventilated lung to be colder than desired.

The unilateral lung ventilation system 10 of the present invention could also be used to treat the lungs for injury by delivering anti-inflammatory or other preservative agents to either one, or both of, the non-ventilated lung (i.e., via the catheter 36) and the ventilated lung (i.e., via the main channel 20 of the tube 12). The unilateral lung ventilation system 10 of the present invention could also be used to individually treat the lungs with agents designed to restore lung function, including, but not limited to, exogenous surfactant therapies.

The triple-lumen construction of the catheter 36 of system 10 provides two additional lumens 40 in addition to the lumen 40 dedicated to inflation/deflation of the balloon mechanism 34 that are available for conveying a therapeutic agent or a device (e.g., a guiding stylet) to the non-ventilated lung. Potential treatments or treatment combinations using the two additional lumens 40 of catheter 36 include, but are not limited to, (1) pressure support and drug delivery or (2) constant flow of a gas/medium (warm or cold) using an inlet and outlet, with or without a drug delivery through the inlet port.

What is claimed is:

1. A system for unilateral lung ventilation comprising:
an endotracheal tube having a primary wall defining as main channel for delivering a ventilation medium to the trachea of a patient and an inner channel disposed within the main channel and separated along its length from the main channel by a secondary wall connected to the primary wall, the inner channel having a first end opening into the main channel and an opposite second end aligned with a distal end of the main channel; and
a blocking device including an inflatable member having inflated and deflated conditions and adapted for inflation within the mainstem bronchus of a non-ventilated one of a patient's lungs such that the ventilation medium from the endotracheal tune is prevented from entering the non-ventilated lung, the blocking device also including an elongated catheter supporting the inflatable member and having an inflation lumen adapted to deliver an inflation medium to the inflatable member;
the catheter further including at least one lung treatment lumen adapted for delivery of a treatment agent into the non-ventilated lung when the inflatable member is inflated within the mainstem bronchus of the non-ventilated lung;
wherein the inner channel of the endotracheal tube is adapted for receipt of the catheter and the inflatable member when the inflatable member is in the deflated condition to provide a guideway to facilitate passage of the catheter and the inflatable member to a distal end of the endotracheal tube, such that when the catheter is positioned within the inner channel the catheter does not disturb ventilation medium flowing in the main channel; and
wherein the endotracheal time further comprises:
a side branch connected to the primary wall of the endotracheal tube so as to be in communication with the inner channel, the side branch and the inner channel of the endotracheal tube joining at a junction positioned distal to the first end of the inner channel, the side branch being adapted for receipt of the catheter and the inflatable member of the blocking device to direct the catheter and the inflatable member into the inner channel of the endotracheal tube; and
a valve configured to selectively close off at least one of the side branch and the inner channel at the junction depending on whether or not the blocking device is installed, wherein the valve is configured to substantially close off an end of the side branch at the junction when the blocking device is removed from the inner channel of the endotracheal tube, thereby providing for parallel flow of a ventilation medium through the endotracheal tube in both the main channel and the inner channel of the endotracheal tube.

2. The unilateral lung ventilation system according to claim 1, wherein the catheter of the blocking device includes a plurality of lung treatment lumens.

3. The unilateral lung ventilation system according to claim 1, wherein the valve is configured to substantially close of the inner channel when the blocking device is inserted into the inner channel, thereby substantially preventing a ventilation medium introduced into the main channel from flowing through the inner channel.

4. A system for unilateral lung ventilation comprising:
an endotracheal tube having a primary wall defining a main channel for delivering a ventilation medium to the trachea of a patient, the endotracheal tube also having a secondary wall defining an inner channel located within the main channel, the secondary wall being connected to the primary wall; and
a blocking device including an inflatable member having inflated and deflated conditions and adapted for inflation within the mainstem bronchus of a non-ventilated one of the lungs of the patient such that the ventilation medium from the endotracheal tube is prevented from entering the non-ventilated lung, the blocking device also including an elongated catheter supporting the inflatable member and adapted to deliver an inflating medium to the inflatable member;
wherein in a first state, the blocking device is not installed in the endotracheal tube;
wherein in a second state, the blocking device is installed through the inner channel of the endotracheal tube with the catheter extending through the inner channel so as to not disturb ventilation medium flowing in the main channel and the inflatable member positioned beyond a distal end of the endotracheal tube; and
wherein the endotracheal tube further comprises:
a side branch connected to the primary wall of the endotracheal tube so as to be in communication with the inner channel, the side branch and the inner channel joining at a junction, wherein in the second state, the catheter extends through the side branch into the inner channel of the endotracheal tube; and
a valve located at the junction between the side branch and the inner channel, wherein in the first state, the valve substantially closes off the side branch at the junction, thereby providing for parallel flow of a ventilation medium through the endotracheal tube in both the main channel and the inner channel of the endotracheal tube.

5. The unilateral lung ventilation system according to claim 4, wherein the side branch is oriented at an oblique angle with respect to the primary wall.

6. The unilateral lung ventilation system according to claim 4, wherein in the second state, the valve substantially closes off the inner channel of the endotracheal tube, thereby preventing a ventilation medium in the main channel from circulating through the inner channel.

7. The unilateral lung ventilation system according to claim 4, wherein the catheter of the blocking device includes a lumen for delivering an inflation fluid to the inflatable member of the blocking device and at least one additional lumen for delivering a therapeutic agent to the non-ventilated lung when the inflatable member of the blocking device is inflated in the mainstem bronchus of the non-ventilated lung.

8. A method of unilaterally ventilating a patient such that the patient has a ventilated lung and a non-ventilated lung, the method comprising the steps of;
providing an endotracheal tube having a main channel for delivering a ventilation medium to the trachea of the patient and an inner channel located within the main channel, the inner channel having a proximal end open to the main channel and being separated along its length from the main channel by a secondary wall connected to a primary wall that defines the main channel;
providing a blocking device including an inflatable member having inflated and deflated conditions and adapted to receive an inflation fluid for inflation of the inflatable member within the mainstem bronchus of the non-ventilated lung, the blocking device including an elongated catheter supporting the inflatable member and having an inflation fluid lumen adapted for delivery of the inflation fluid to the inflatable member;

the catheter further including at least one lung treatment lumen adapted for delivery of a treatment agent into the non-ventilated lung when the inflatable member is inflated within the mainstem bronchus of the non-ventilated lung;

the endotracheal tube further including a valve for selectively blocking the inner channel depending on the presence of the blocking device;

inserting the endotracheal tube into the patient via the patient's mouth such that a distal end of the tube is received in the trachea of the patient;

inserting the blocking device through the inner channel of the endotracheal tube into the patient via the patient's mouth with the inflatable member in the deflated condition such that the inflatable member is received b the mainstem bronchus of the non-ventilated lung of the patient, which insertion of the blocking device through the inner channel actuates the valve, thereby preventing the ventilation medium delivered to the main channel from flowing through the inner channel while the blocking device remains inserted;

delivering the inflation fluid to the inflatable member via the inflation fluid lumen of the catheter to inflate the inflatable member to the inflated condition;

delivering a ventilation medium into the trachea of the patient via the main channel of the endotracheal tube to ventilate the ventilated lung undisturbed by the catheter of the blocking device which is located in the inner channel apart from the main channel; and delivering a therapeutic agent to the non-ventilated lung via the at least one lung treatment lumen.

9. The method according to claim 8, wherein the therapeutic agent delivered to the non-ventilated lung is cooled air.

10. The method according to claim 8, wherein the therapeutic agent delivered to the non-ventilated lung is a preservative agent.

11. The method according to claim 8, wherein the therapeutic agent delivered to the non-ventilated lung is an anti-inflammatory agent.

12. The method according to claim 8 further comprising the step of delivering a therapeutic agent to the ventilated lung.

13. The method according, to claim 12, wherein the therapeutic agent delivered to the non-ventilated lung is cooled air and the therapeutic agent delivered to the ventilated lung is nitric oxide to maintain a ventilation/perfusion (V/Q) matching.

14. The method according to claim 8, further comprising:

actuating the valve to open the inner channel by removal of the blocking device from the inner channel, thereby allowing the ventilation medium delivered to the main channel to flow through the inner channel while the blocking device remains removed.

* * * * *